(12) United States Patent
Saito et al.

(10) Patent No.: US 8,518,009 B2
(45) Date of Patent: Aug. 27, 2013

(54) DISPOSABLE DIAPER

(75) Inventors: Kyota Saito, Kagawa (JP); Seiichi Kuwano, Kagawa (JP); Yoshio Ono, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 295 days.

(21) Appl. No.: 12/935,495

(22) PCT Filed: Feb. 19, 2009

(86) PCT No.: PCT/JP2009/052839
§ 371 (c)(1),
(2), (4) Date: Dec. 6, 2010

(87) PCT Pub. No.: WO2009/122803
PCT Pub. Date: Oct. 8, 2009

(65) Prior Publication Data
US 2011/0106039 A1 May 5, 2011

(30) Foreign Application Priority Data

Mar. 31, 2008 (JP) ................... 2008-093772
Mar. 31, 2008 (JP) ................... 2008-093773

(51) Int. Cl.
*A61F 13/20* (2006.01)
*A61F 13/15* (2006.01)

(52) U.S. Cl.
USPC .................. 604/385.3; 604/385.29

(58) Field of Classification Search
USPC ................ 604/358–400
See application file for complete search history.

(56) References Cited

U.S. PATENT DOCUMENTS

| | | | |
|---|---|---|---|
| 5,749,865 A * | 5/1998 | Yamamoto et al. | 604/385.29 |
| 2004/0030317 A1* | 2/2004 | Torigoshi | 604/385.27 |
| 2007/0073259 A1* | 3/2007 | Erdman et al. | 604/385.28 |
| 2007/0208317 A1* | 9/2007 | Krautkramer et al. | 604/385.3 |

FOREIGN PATENT DOCUMENTS

| | | |
|---|---|---|
| JP | 08-84747 | 4/1996 |
| JP | 2001-29388 | 2/2001 |
| JP | 2001-314441 | 11/2001 |
| JP | 2002-45399 | 2/2002 |
| JP | 2002-248127 | 9/2002 |
| JP | 2004-298395 | 10/2004 |
| JP | 2004-298399 | 10/2004 |
| JP | 2007-511326 | 5/2007 |
| JP | 2009-82482 | 4/2009 |

* cited by examiner

*Primary Examiner* — Jackie Ho
*Assistant Examiner* — Peter S Vasat
(74) *Attorney, Agent, or Firm* — Brinks Hofer Gilson & Lione

(57) ABSTRACT

A disposable diaper having a front waist region including elasticized regions extending at least in the transverse direction Y, wherein the elasticized regions comprise a first elasticized region defined between a waist-opening peripheral edge and a front end flap of the absorbent chassis so as to extend in the transverse direction Y. A second elasticized region is defined adjacent the first elasticized region so as to extend in the transverse direction Y, and a pair of third elasticized regions are defined adjacent the second elasticized region and spaced from and opposed to in the transverse direction Y on both sides of a non-elasticized region formed in a transverse middle of the front waist region. The second elasticized region extends across the front flap of the absorbent chassis.

18 Claims, 11 Drawing Sheets

FIG.4
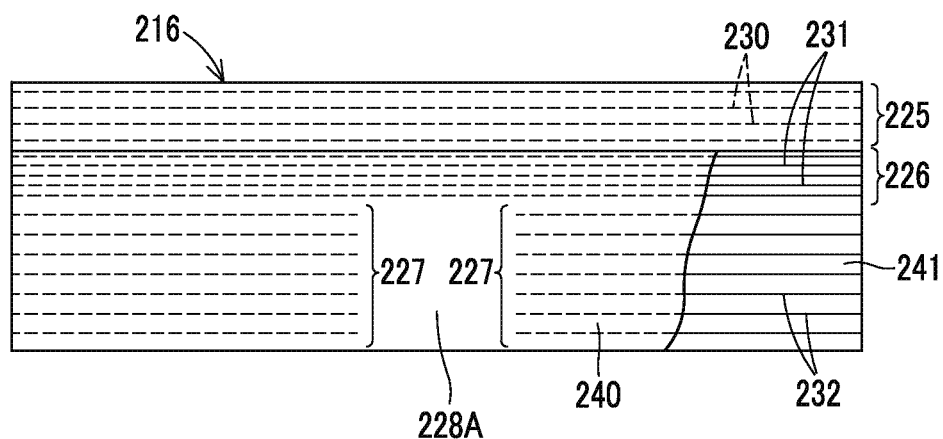
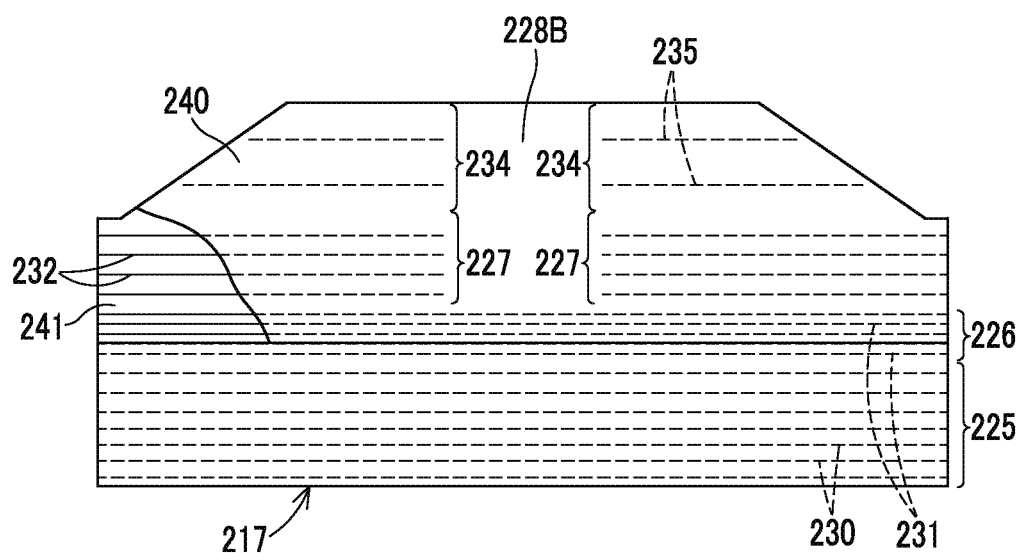

DISPOSABLE DIAPER

TECHNICAL FIELD

The present invention relates to a disposable diaper improved particularly in fit and appearance thereof.

RELATED ART

Disposable diapers provided in front and rear waist regions with a plurality of waist elastic elements extending circumferentially with respect to these waist regions to ensure good fitness to the wearer's body are well known. For example, JP 2002-248127 A (PATENT DOCUMENT 1) discloses, as shown in FIG. 11A, 11B of the accompanying drawings, a disposable diaper 110 comprising front and rear waist regions, a crotch region, an absorbent chassis 112 attached to the inner surface of a waist member 111, a plurality of waist elastic elements 126 extending along a peripheral edge 116a of a waist-opening and spaced from one another in a longitudinal direction at a given pitch and waist elasticized elements extending in a transverse direction from respective pairs of opposite side edges of the front and rear waist regions to respective side edges of the absorbent chassis 112.
PATENT DOCUMENT 1: JP 2002-248127 A

DISCLOSURE OF THE INVENTION

Problem to be Solved by the Invention

According to the invention as disclosed in PATENT DOCUMENT 1, the waist elastic elements 126 extend not across the absorbent chassis 112. Consequentially, contractile force of waist elastic elements 130 does not act directly upon an absorbent core 144 contained by the absorbent chassis 112 and the absorbent core 144 is substantially free from getting wrinkles. As a result, the absorbing capacity thereof would not be significantly reduced.

However, with the diaper 110 put on the wearer's body, a space S is formed between the wearer's body A and the front end flap 162 of the absorbent chassis 112, i.e., the region of the absorbent chassis 112 in which the absorbent core 144 is not present, as will be apparent from FIG. 11A of the accompanying drawings. This is for the reason that the absorbent core 144 typically contains fluff pulp for the purpose of improvement in liquid-absorbing capacity as well as dispersant capacity thereof and has a given thickness larger than that of the front end flap 162 consisting of only the sheet member. Such differential thickness inevitably causes the region defined between the waist-opening's periphery 116a provided with the waist elastic elements 126 so as to be brought into close contact with the wearer'body A and the absorbent core 144 to be spaced from the wearer's body A. Particularly when a large quantity of urine is absorbed by the absorbent core 144, the thickness of the absorbent core 144 will further increase and the space S will be correspondingly enlarged.

If the wearer changes his or her posture, e.g., bends him- or herself forward from the above-described situation, the wearer's body A depresses the waist-opening's periphery 116a and the vicinity thereof forward so as to fold the front end flap 162 and the region of the waist member 111 opposed to the front end flap 162 toward the space S. As a result, the front end flap 162 and the region of the waist member 111 are displaced together downward into the interface between the wearer's body A and the absorbent core 144, as shown by FIG. 11B, resulting in formation of a step R.

Even assumed that the front end flap 162 is provided with the waist elastic elements 126, the absorbent core 144 will have its thickness increased as a large quantity of urine is absorbed by the absorbent core 144 and, in consequence, the front end of the absorbent core 144 and the region of the waist member 111 opposed thereto will be displaced together upward on the front end flap 162 held till then in close contact with the wearer's body A. In this case also, the situation similar to that as shown by FIG. 11B due to displacement of the front end flap 162 and the region of the waist member opposed thereto downward into the space S might occur.

The step R not only disfigures the diaper 110 but also causes body waste to leak out due to, for example, an excessive quantity of urine for the absorbent core 144 accumulated in the step R.

In view of the problem as has been described just above, it is a principal object of the present invention on a first aspect thereof to provide a disposable diaper improved so as to, with the diaper put on the wearer's body, prevent at least the front end of the absorbent chassis and the region of the front waist panel opposed thereto from being displaced downward into the interface between the wearer's body and the absorbent core possibly to form the step defined by a part of the front waist region and eventually to cause body waste to leak out, on one hand, and so as to have a good appearance, on the other hand.

In further view of the problem as has been described above, it is a principal object of the present invention on a second aspect thereof to provide a disposable diaper improved so as to, with the diaper put on the wearer's body, the front waist region prevent from being partially formed with the step due to downward displacement of the front end flap of the absorbent chassis or upward displacement of the absorbent core and thereby to prevent body waste from leaking out, on one hand, and so as to have a good appearance, on the other hand.

Measure to Solve the Problem

The present invention includes first and second aspects.

The object set forth above is achieved, according to the present invention on the first aspect thereof, by an improvement in a disposable diaper having a longitudinal direction, a transverse direction, a side facing the wearer's skin, a side facing away from the wearer's skin, a front waist region, a rear waist region, a crotch region extending between the front and rear waist regions, a waist-opening, a pair of leg-openings, and comprising an annular elasticized waist panel defining the front and rear waist regions and an absorbent chassis joined to front and rear halves of the waist panel so as to extend across the crotch region into the front and rear waist regions and including an absorbent core and front and rear end flaps extending from front and rear ends of the absorbent core in the longitudinal direction.

The improvement according to the present invention on the first aspect thereof is characterized in that at least the front waist region of the front and rear waist regions includes elasticized regions extending at least in the transverse direction, the elasticized regions comprise a first elasticized region defined between a periphery of the waist-opening and a vicinity of the front end flap of the absorbent chassis so as to extend in the transverse direction, second elasticized regions defined adjacent the first elasticized region so as to extend in the transverse direction and a pair of third elasticized regions defined adjacent the second elasticized regions so as to extend from the opposite side edges of the front waist region to the opposite side edges of the absorbent chassis and to be spaced from and opposed to each other in the transverse direction on both sides of the non-elasticized region defined in a transverse middle of the front waist region, and the second elasticized region extends across the front end flap of the absorbent chassis.

The invention on the first aspect thereof further includes preferred embodiments as follow:

(1) The second elasticized region has a tensile stress same as or higher than a tensile stress of the first elasticized region.
(2) A relationship among the first elasticized region, the second elasticized region and the third elasticized regions can be represented in the form of the second elasticized region≧the first elasticized region>the third elasticized regions.
(3) The first elasticized region, the second elasticized regions and the third elasticized regions are respectively provided with a plurality of strand-like elastic elements extending in the transverse direction wherein the waist elastic elements used to form the first elasticized region have an elongation percentage equal to that of the waist elastic elements used to form the second elasticized regions.
(4) The first elasticized region, the second elasticized region and the third elasticized regions are respectively provided with a plurality of strand-like elastic elements extending in the transverse direction wherein all of these waist elastic elements are formed by the same elastic elements.

The object set forth above is achieved, according to the present invention on the second aspect thereof, by an improvement in a disposable diaper having a longitudinal direction, a transverse direction, a side facing the wearer's skin, a side facing away from the wearer's skin, a front waist region, a rear waist region, a crotch region extending between the front and rear waist regions, a waist-opening, a pair of leg-openings, an annular elasticized waist panel defining the front and rear waist regions and an absorbent chassis comprising an absorbent panel joined to front and rear halves of the waist panel so as to extend across the crotch region into the front and rear waist regions and including an absorbent core and front and rear end flaps extending from front and rear ends of the absorbent panel in the longitudinal direction.

The improvement according to the invention on the second aspect thereof is characterized in that at least the front waist region of the front and rear waist regions includes elasticized regions extending at least in the transverse direction, the elasticized regions comprise a first elasticized region defined between a periphery of the waist-opening and a front end of the absorbent chassis inclusive of the front end flap so as to extend in the transverse direction, a pair of second elasticized regions defined adjacent the first elasticized region so as to extend from opposite side edges of the front waist region to opposite side edges of a front end of the absorbent panel and to be spaced from and opposed to each other in the transverse direction on both sides of a first non-elasticized region defined in a transverse middle of the front waist region and a pair of third elasticized regions defined adjacent the second elasticized regions so as to extend from the opposite side edges of the front waist region to the opposite side edges of the front end of the absorbent panel and to be spaced from and opposed to each other in the transverse direction on both sides of the first non-elasticized region, and the first elasticized region extends across the front end of the absorbent panel.

The present invention on the second aspect thereof further includes preferred embodiments as follow:

(1) The second elasticized region has a tensile stress same as or higher than a tensile stress of the first elasticized region.
(2) A relationship among the first elasticized region, the second elasticized region and the third elasticized regions can be represented in the form of the second elasticized region≧the first elasticized region>the third elasticized regions.
(3) The first elasticized region, the second elasticized regions and the third elasticized regions are respectively provided with a plurality of strand-like elastic elements extending in the transverse direction wherein all of these waist elastic elements are formed by elastic elements which have a common elongation percentage.
(4) The first elasticized region, the second elasticized region and the third elasticized regions are respectively provided with a plurality of strand-like elastic elements extending in the transverse direction wherein all of these waist elastic elements are formed by same elastic elements.
(5) Elasticized regions in the rear waist region comprise a fourth elasticized region defined between opposite side edges of the rear waist region so as to extend along the periphery of the waist-opening in the transverse direction, a fifth elasticized region defined adjacent the fourth elasticized region so as to extend to the rear end of the absorbent panel, a pair of sixth elasticized regions defined adjacent the fifth elasticized region so as to be spaced from and opposed to each other in the transverse direction on both sides of a second non-elasticized region formed in a transverse middle of the rear waist region and a pair of seventh elasticized regions defined adjacent the sixth elasticized regions so as to be spaced from and opposed to each other in the transverse direction on both sides of the second non-elasticized region wherein the sixth elasticized regions have a tensile stress higher than that of the seventh elasticized regions and respective tensile stresses of the fourth elasticized region and the fifth elasticized region are higher than that of the sixth elasticized region.

Effect of the Invention

According to the invention on the first aspect thereof, at least the front waist region of the front and rear waist regions is provided with the waist elastic elements extending in the transverse direction across the front end flap of the absorbent chassis so that the tensile stress of these elastic elements biases the front end flap in a close contact with the wearer's body. With this unique arrangement, the front end flap would not be displaced downward into the interface between the wearer's body and the absorbent core and thereby any quantity of body waste is prevented from leaking out from the diaper, on one hand, and the disposable diaper having good appearance can be obtained, on the other hand.

According to the invention on the second aspect thereof, the first elasticized region extends across the front end flap of the absorbent chassis and the front end of the absorbent panel. With this unique arrangement, it is possible to obtain a disposable diaper improved so that, with the diaper put on the wearer's body, the front waist region would not be partially formed with the step due to downward displacement of the front end flap of the absorbent chassis or upward displacement of the absorbent panel and thereby body waste is prevented from leaking out, on one hand, and the diaper can have a good appearance, on the other hand.

BRIEF DESCRIPTION OF THE DRAWINGS

[FIG. 4] Plan view corresponding to FIG. 2 devoid of the absorbent chassis.

Figure 1:
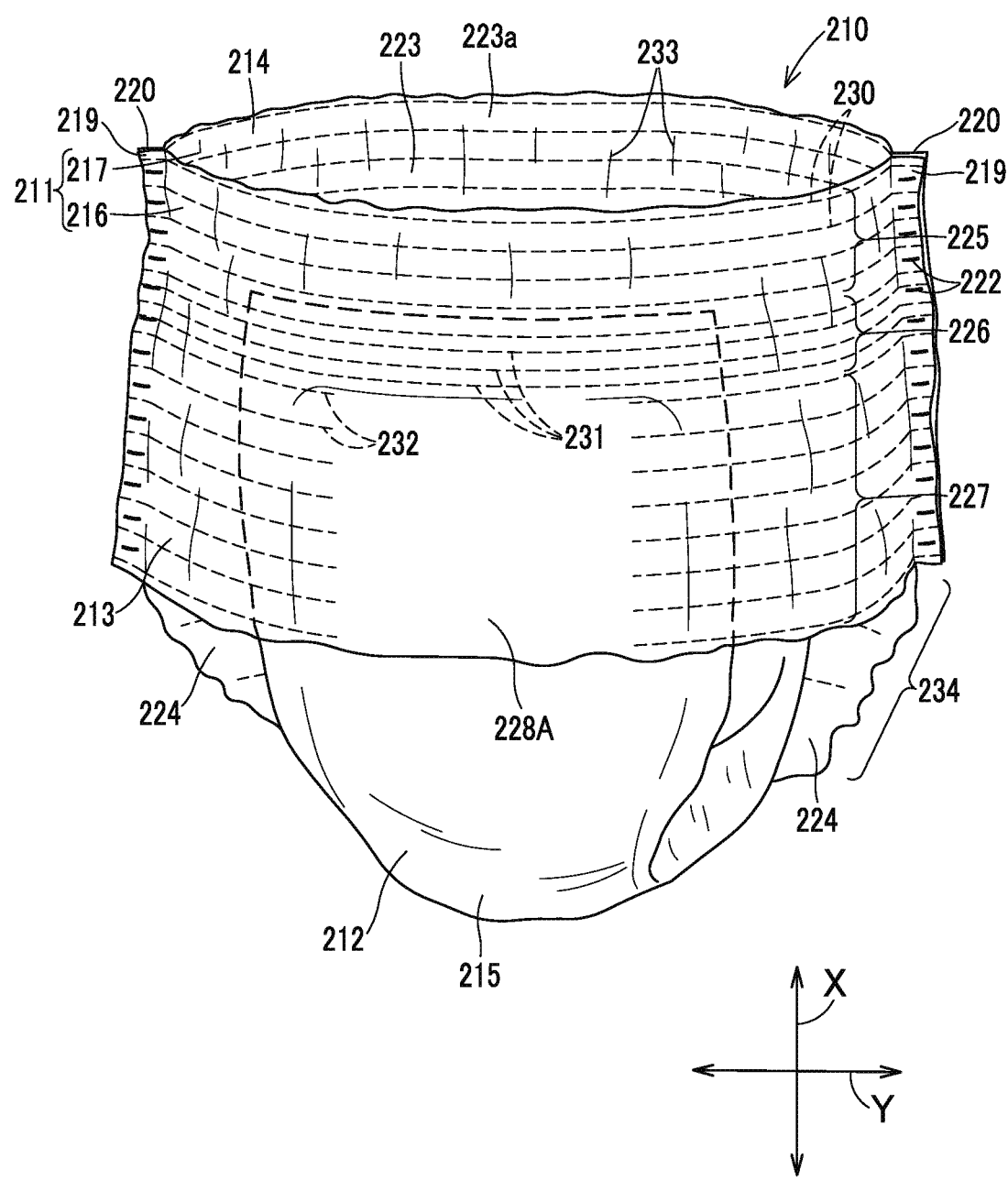
[FIG. 1] Perspective view of the disposable diaper according to the invention on the first aspect thereof.

IDENTIFICATION OF REFERENCE NUMERALS USED IN THE DRAWINGS 210 diaper
211 elasticized waist panel
212 absorbent chassis
213 front waist region
214 rear waist region
215 crotch region
219 opposite side edges of the front waist region
220 opposite side edges of the rear waist region
223 waist-opening
223a waist-opening's periphery
224 leg-opening
225 first elasticized region
226 second elasticized region
227 third elasticized region
228A non-elasticized region (first non-elasticized region)
230 first waist elastic element
231 second waist elastic element
232 third waist elastic element
262 front end flap
263 rear end flap
310 diaper
311 elasticized waist panel
312 absorbent chassis
313 front waist region
314 rear waist region
315 crotch region
316 waist-opening
317 leg-opening
318c opposite side edge of the front waist panel
326 first waist elastic element
327 second waist elastic element
328 third waist elastic element
329 fourth waist elastic element
330 fifth waist elastic element
331 sixth waist elastic element
332 seventh waist elastic element
333 first elasticized region
334 second elasticized region
335 third elasticized region
336 fourth elasticized region
337 fifth elasticized region
338 sixth elasticized region
339 seventh elasticized region
340A, 340B non-elasticized region
344 absorbent core
346 absorbent panel
346a front end of the absorbent panel
346b rear end of the absorbent panel
346c side edge of the absorbent panel
347 front end region 347 of the absorbent panel
348 rear end region 347 of the absorbent panel

DETAILED DESCRIPTION OF THE PREFERRED EMBODIMENTS

The invention on the first aspect will be exemplarily described with reference to the accompanying drawings.

Figure 2:
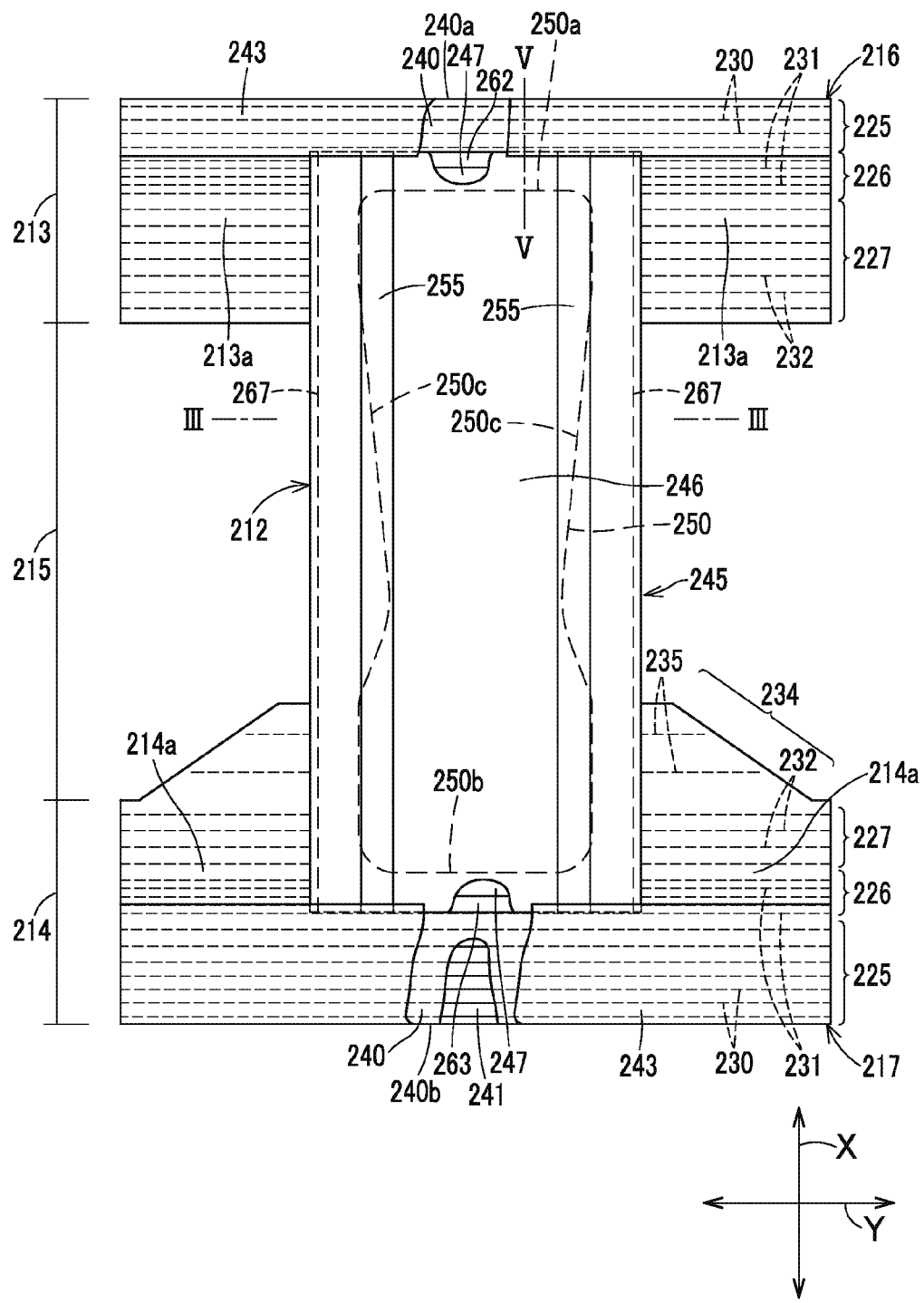
[FIG. 2] Plan view of the flatly developed disposable diaper.
Figure 3:
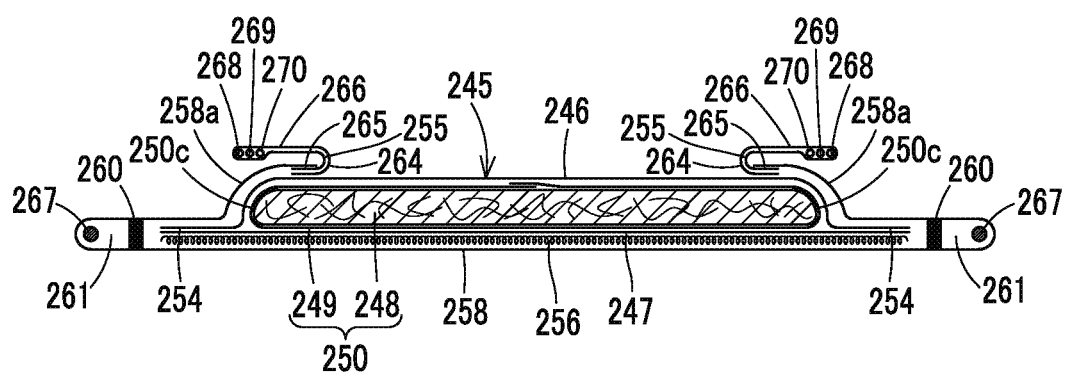
[FIG. 3] Sectional view taken along the line III-III in FIG. 2.

FIG. 1 is a perspective view of a diaper 210 put on the wearer's body. FIG. 2 is a partially cutaway plan view of the flatly developed diaper 210 in a longitudinal direction X as well as in a transverse direction Y after front and rear waist regions have been peeled off from each other along seams 222 in the longitudinal direction. FIG. 3 is a sectional view taken along a line III-III in FIG. 2. FIG. 4 is a partially cutaway plan view corresponding to FIG. 2 devoid of an absorbent chassis 212.

As shown in FIG. 1, the diaper 210 comprises an annular elasticized waist panel 211, an absorbent chassis 212 attached to the side of the annular elasticized waist panel 211 facing the wearer's skin, a front waist region 213, a rear waist region 214 and a crotch region 215 extending in the longitudinal direction X between the front and rear waist regions 213, 214.

The elasticized waist panel 211 comprises, in turn, a rectangular front waist panel 216 defining the front waist region 213 and a substantially trapezoidal rear waist panel 217 defining the rear waist region 214 and a part of the crotch region 215. The front waist panel 216 and the rear waist panel 217 are put flat together along respective pairs of opposite side edges (i.e., respective pairs of opposite side edges of the front and rear waist regions) 219, 220 and joined together along seams 222 arranged intermittently in the longitudinal direction X by well known means such as heat embossing, supersonic sealing or the other heat sealing techniques so as to define a waist-opening 223 and a pair of leg-openings 224.

As will be apparent from FIGS. 1 and 4, the front and rear waist regions 213, 214 comprise a first elasticized region 225 extending along a waist-opening's periphery 223a in the transverse direction Y, a second elasticized region 226 defined adjacent the first elasticized region 225 so as to extend across a front end of the absorbent chassis 212, and a pair of third elasticized regions 227 spaced from and opposed to each other on both sides of first and second non-elasticized regions 228A, 228B defined in respective transverse middles of the front and rear waist regions 213, 214 wherein the respective elasticized regions 225, 226, 227 are provided with strand-like waist elastic elements 230, 231, 232, respectively.

Specifically, the first elasticized region 225 is provided with a plurality of first waist elastic elements 230 extending along the waist-opening's periphery 223a, the second elasticized region 226 is provided with a plurality of second waist elastic elements 231 extending across the absorbent chassis 212 in the transverse direction Y, and the third elasticized regions 227 are provided with a plurality of third waist elastic elements 232 extending in the transverse direction Y on transversely opposite lateral zones 213a, 214a of the front and rear waist regions 213, 214, respectively. Under contraction of these waist elastic elements 230, 231, 232, the diaper 210 is formed on its surface with a plurality of gathers 233 (See FIG. 1). It should be appreciated that a desired effect can be achieved by at least the first non-elasticized region 228A of the first and second non-elasticized regions 228A, 228B. The region in the rear waist panel 217 defining a part of the crotch region 215 is formed on both sides of the second non-elasticized region 228B with a pair of fourth elasticized regions 234 spaced from each other in the transverse direction Y wherein the fourth elasticized regions 234 are provided with a plurality of fourth waist elastic elements 235 extending in the transverse direction Y.

As shown in FIGS. 2 and 3, the front and rear waist panels 216, 217 are formed by an inner layer sheet 240 lying on the side facing the wearer's skin and an outer layer sheet 241 lying on the side facing from the wearer's skin. The outer layer sheet 241 has prolongations 243 extending outward from front and rear edges 240a, 240b of the inner layer sheet 240 in the longitudinal direction X wherein these prolongations 243 are folded back on the side facing the wearer's skin and joined to the lateral zones 213a, 214a after the absorbent chassis 212 has been attached to the respective inner sides of the front waist panel 216 and the rear waist panel 217. The prolongations 243 of the outer layer sheet 241 cover the front and rear ends 240a, 240b in this manner and thereby body waste can be prevented from leaking out beyond the front and rear ends 240a, 240b.

Suitable stock material for the inner layer sheet 240 and the outer layer sheet 241 includes hydrophobic fibrous nonwoven fabric, moisture-pervious plastic film and laminate sheet thereof.

The waist elastic elements 230, 231, 232, 235 are sandwiched between the inner layer sheet 240 and the outer layer sheet 241 and stretchably attached to the inner surface of at least the inner layer sheet 240 of the both sheets 240, 241 by hot melt adhesive (not shown). It should be noted here that none of the waist elastic elements 230, 231, 232, 235 is provided between the inner layer sheet 240 and the outer layer sheet 241 in the first and second non-elasticized regions 228A, 228B.

As shown by FIGS. 2 and 3, the absorbent chassis 212 includes an absorbent structure 245. The absorbent structure 245 comprises, in turn, a liquid-pervious liner 246 facing the wearer's skin (i.e., topsheet), a liquid-impervious backsheet 247, an absorbent panel 250 comprising an absorbent core 248 having an adequate bodily fluid absorbing capacity and a liquid-dispersant sheet 249 used to wrap an absorbent core 248.

The liquid-absorbent structure 245 comprises a pair of end flaps formed by bonding portions of the backsheet 247 extending outward beyond the front and rear ends 250a, 250b of the absorbent panel 250 in the longitudinal direction X to portions of the liner 246 facing the wearer's skin extending outward further than the backsheet 247 in the longitudinal direction X by hot melt adhesive (not shown) so as to extend in the transverse direction Y, a pair of inner side flaps 254 formed by bonding portions of the liner 246 facing the wearer's skin extending outward beyond a pair of side edges 250c of the absorbent panel 250 in the transverse direction Y to the corresponding portions of the backsheet 247 so as to extend in the longitudinal direction X, and a pair of barrier leg-cuffs 255 extending in the longitudinal direction X along opposite side edges of the liquid-absorbent structure 245.

The absorbent chassis 212 further includes a first sheet member 258 fixed to a lower surface of the liquid-absorbent structure 245 via a hot melt adhesive coated region 256 and a pair of sleeve-like outer side flaps 261 each comprising a region (prolongation) 258a of the first sheet member 258 extending outward beyond the liquid-absorbent structure 245 in the transverse direction Y, then folded back inward so as to define two layers placed upon each other, which are bonded to each other by hot melt adhesive 260. Each of these outer side flaps 261 is adapted to cover the outer side edge of the associated inner side flap 254. By cover the outer side edges of the respective inner side flaps 254 with the respective outer side flaps 261, it is ensured to prevent the outer side edges of the respective inner side flaps 254 which have conventionally been exposed in the form of relative sharp cut ends from coming in contact with and irritating the wearer's skin, causing itch and/or rash.

The absorbent chassis 212 further includes the front and rear end flaps 262, 263 defined by portions of the liner 246 facing the wearer's skin extending outward beyond the backsheet 247 in the longitudinal direction X and the front and rear ends of the first sheet member 258, respectively. These front and rear end flaps 262, 263 can be formed in this manner since the first sheet member 258 has previously been fixed to the lower surface of the liquid-absorbent structure 245.

To inner walls of the sleeves defined by the respective outer side flaps 261, strand-like elastic elements 267 extending stretchably/contractibly in the longitudinal direction X are attached by hot melt adhesive (not shown). With the diaper 210 put on the wearer's body, the outer side flaps 261 are curved inwardly as viewed in the transverse direction Y under contraction of the elastic elements 267 so as to be elastically pressed against the wearer's thighs. While each of the sleeves is provided with the single elastic element 267 so far as the illustrated embodiment is concerned, it is possible to provide each of the sleeves with two or more elastic elements 267.

Each of the barrier leg-cuffs 255 is formed by the prolongation 258a of the first sheet member 258 and the second sheet member 264 folded in two wherein the folded end of the second sheet member 264 is fixed to the prolongation 258a by hot melt adhesive (not shown) to define a fixed edge 265 and the distal end of the second sheet member 264 is folded back to define a sleeve-like free edge 266. With the diaper 210 flatly developed, the free edge 266 faces the associated prolongation 258a of the first sheet member 258 and the free edge 266 is provided on its inner surface with three elastic elements 268, 269, 270 permanently bonded thereto by hot melt adhesive (not shown) so as to extend in the longitudinal direction X. With the diaper 210 put on the wearer's body, the elastic elements 268, 269, 270 are sufficiently stretched to be spaced from the associated prolongation 258a of the first sheet member 258 and thereby to prevent body waste from leaking out beyond the associated lateral region of the absorbent chassis 212.

While each of the free edges 266 is provided within the sleeve defined thereby with three elastic elements 268, 269, 270 in the case of the illustrated embodiment, the sleeve defined by the free edge 266 may be provided with at least one elastic element so far as this single elastic element has a tensile stress sufficient to space the free edge 266 from the associated prolongation 258a of the first sheet member 258. These elastic elements 268, 269, 270 may be replaced by an elastically contractible single sheet having a required width as the second sheet member 264.

In the absorbent panel 250, the absorbent core 248 comprises fluff pulp, super-absorbent polymer (SAP) and, if desired, heat sealable staple fiber mixed together and wrapped with the liquid-dispersant sheet 249 as a whole. By wrapping the absorbent core 248 as a whole with the liquid-dispersant sheet 249 in this manner, the absorbent core 248 can be protected from getting out of its desired shape and falling off of SAP. To improve the shape retention and the liquid dispersion, the absorbent core 248 is compressed to have a concave-shaped contour curved inwardly and provided with rigidity sufficiently higher than that of the sheet members constituting the diaper 210 to be sometimes referred to as "semi-rigid".

Figure 5:
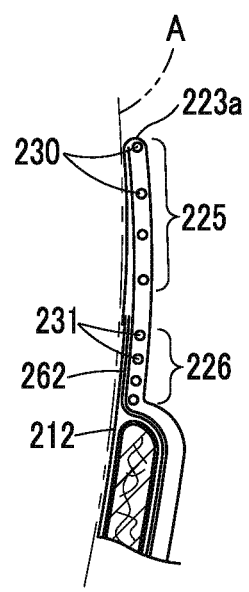
[FIG. 5] Schematic sectional view taken along a line V-V in FIG. 2, showing the disposable diaper put on the wearer's body.

FIG. 5 is a schematic sectional view taken along a line V-V in FIG. 2, assuming that the disposable diaper 210 has been put on the wearer's body. FIG. 11 is a schematic sectional view corresponding to FIG. 5 showing the disposable diaper 110 of prior art.

As shown in FIG. 5, the second elasticized region 226 of the front waist region 213 is provided with second waist elastic elements 231 extending across the front flap 262 of the absorbent chassis 212 in the transverse direction Y. The second waist elastic elements 231 extending across the front end flap 262 of the absorbent chassis 212 in this manner make it possible to prevent the front waist panel 216 from being partially formed with a step.

Figure 11A:
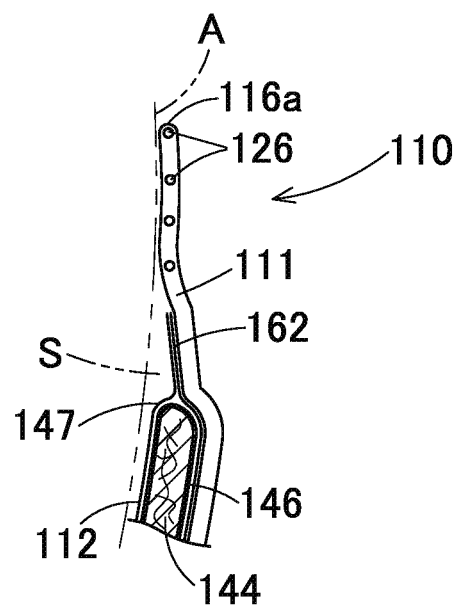
[FIG. 11] Schematic sectional views A and B corresponding to FIGS. 5 and 10 assuming that the disposable diaper of prior art has been put on the wearer's body.

In the case of the conventional disposable diaper 110, as will be apparent from FIG. 11A, a space S has been inevitably formed between the front end flap 162 of the absorbent chassis 112 and the wearer's body A. This is for the reason that the absorbent core 144 typically contains fluff pulp for the purpose of improvement in liquid-absorbing capacity as well as dispersant capacity thereof and has a given thickness larger than that of the front end flap 162 consisting of only the sheet member. Such differential thickness inevitably causes the region defined between the waist-opening's periphery 116a provided with the waist elastic elements 126 so as to be brought into close contact with the wearer' body A and the absorbent core 144 to be spaced from the wearer's body A. Particularly when a large quantity of urine is absorbed by the absorbent core 144, the thickness of the absorbent core 144 will further increase and the space S will be correspondingly enlarged.

Figure 11B:
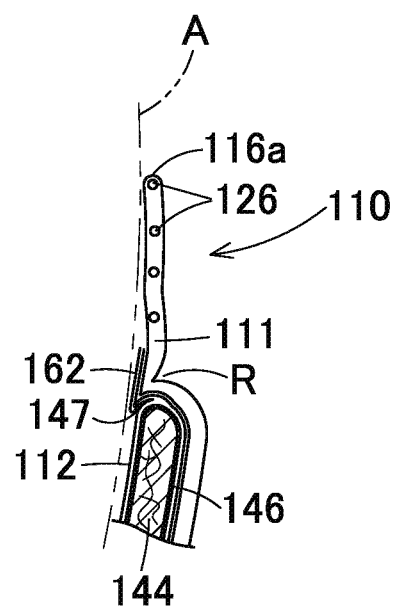

If the wearer changes his or her posture, e.g., bends him- or herself forward from the above-described situation, the wearer's body A depresses the waist-opening's periphery 116a and the vicinity thereof forward with respect to the wearer so as to fold the front end flap 162 and the region of the waist member 111 opposed to the front end flap 162 toward the space S. As a result, the front end flap 162 and the region of the waist member 111 are displaced together downward into the interface between the wearer's body A and the absorbent core 144, as shown by FIG. 11B, resulting in formation of a step R.

The step R may not only cause the diaper 110 to be displaced from its desired position but also may cause an excessive quantity of urine for the absorbent core 144 to be accumulated on the step R and eventually may leak out. In addition, such step R may disfigure the diaper.

Particularly when the annular elasticized waist panels 211 and the absorbent chassis 212 inclusive of the absorbent core 248 are separately formed as in the present embodiment, the absorbent chassis 212 is suspended like a hammock between the annular elasticized waist panels 211. In such situation, the absorbent chassis 212 might be undesirably displaced between the elastic waist panels 211 and a possibility that the step might be formed will be higher than the case of the diaper 210 having the absorbent core 248 sandwiched directly between the elastic waist panels 211.

As shown in FIG. 5, according to the invention on the first aspect, the second elasticized region 226 is provided with the second waist elastic elements 231 so as to extend across the front end flap 262 of the absorbent chassis 212 as shown by FIG. 5, to ensure that the front end flap 262 may be held in close contact with the wearer's body A and the space S maybe not formed between the front end flap 262 and the wearer's body A. In consequence, the second elasticized region 226 would not be displaced downward into the interface between the absorbent core 248 and the wearer's body A.

Should the second elasticized region 226 have a tensile stress lower than a tensile stress of the first elasticized region 225 in such embodiment, the second elasticized region 226 will bend as the wearer bends him- or herself forward and, as a result, the second elasticized region 226 as well as the front end flap 262 will get a bending potential. Eventually the front waist region 213 might partially formed with the step. To avoid such situation, the second elasticized region 226 preferably has its tensile stress equal to or higher than a tensile stress of the first elasticized region 225 so that a fitness of the second elasticized region 226 to the wearer's body should not be adversely affected by stretching of the first elasticized region 225. On the other hand, the first elasticized region 225 must have a tensile stress sufficient to maintain the front and rear waist regions 213, 214 in close contact with the wearer's waist and, to achieve this, the tensile stress of the first elasticized region 225 is preferably higher than that of the third elasticized region 227. Accordingly, a relationship among these elasticized regions 225, 226, 227 are preferably represented in the form of the second elasticized region 226≧the first elasticized region 225>the third elasticized regions 227.

More specifically, the first elasticized region 225 preferably has a tensile stress of 38-42 mN/mm at 65% of the maximum elongation, the second elasticized region 226 preferably has a tensile stress of 42-48 mN/mm at 65% of the maximum elongation and the third elasticized region 227 preferably has a tensile stress of 28-32 mN/mm at 65% of the maximum elongation. If the tensile stress of the second elasticized region 226 at 65% of the maximum elongation is 42 mN/mm or less, it will be no more possible to maintain the front end flap 262 in close contact with the wearer's body A and to achieve the effect as has been described above.

The tensile stress of the respective elasticized regions 225, 226, 227 was measured by a method as follows:

First, the waist regions are peeled off from each other along the seams 222 and the diaper 210 is flatly developed as seen in FIG. 2 and the respective elastic elements 230, 231, 232 are stretched to the maximum elongation in the transverse direction Y. The front waist panel 216 as a whole is cut off from the diaper 210 and then the respective elasticized regions 225, 226, 227 are cut away from this front waist panel 216 to obtain desired test pieces. Based on these test pieces, widths (dimensions in the longitudinal direction Y of the diaper 210) of the respective test pieces are measured. The respective elasticized regions 225, 226, 227 are cut off in the region defined between each pair of the adjacent elastic elements 230, 231, 232 in middles of this region as viewed in longitudinal direction X. Then, each of the test pieces in contracted state is fixed between a pair of chucks of Tensile Tester manufactured by Shimadzu Corporation (a distance between these chucks is initially set to 100 mm and appropriately adjusted depending on the each of the test pieces). Now the test piece is stretched in the transverse direction Y of the diaper 210 at a rate of 100 mm/min and a load (mN) at 65% of the maximum elongation is measured. Thus, tensile stress is calculated for each of the elasticized regions 225, 226, 227 according to an equation:

Measured value (mN)÷region width (mm)=tensile stress.

The second elasticized region 226 preferably has an elongation percentage equal to or higher than an elongation percentage of the first elasticized region 225. This is for the reason that, if the elongation percentage of the second elasticized region 226 is less than the elongation percentage of the first elasticized region 225, the second elasticized region 226 will be apt to be spaced from the wearer's body A under elongation of the first elasticized region 225 to form the undesirable space S, for example, when the wearer bends him- or herself forward and thereby the first elasticized region 225 is further stretched.

The first, second and third waist elastic elements 230, 231, 232 are made of natural or synthetic rubber in the form of strand or tape having rubber elasticity.

More specifically, when the waist elastic elements 230, 231, 232 comprise strand-like rubber elastic elements, the first and second waist elastic elements 230, 231 may have respective sectional area of 550-650 dtex and respective elongation percentage of 250-300% while the third waist elastic element 232 may have a sectional area of 450-500 dtex and an elongation percentage of 300-350%.

It should be noted here that the first waist elastic elements 230 and the second waist elastic elements 231 may comprise the elastic elements have the sectional area and the elongation percentage different from one from another or all of the waist elastic elements 230, 231 and 232 comprise the same elastic elements so far as the respective elasticized regions 225, 226, 227 have the desired tensile stress. In the front waist region 213 of the illustrated embodiment, the number of the first waist elastic elements 230 is four, the number of the second waist elastic elements 231 is five and the number of the third waist elastic elements 232 is seven in the front waist region 213. It should be appreciated here that the number of the elastic elements used in each of the respective elasticized regions 225, 226, 227 as well as the distance (i.e., pitch) between each pair of the adjacent elastic elements in the respective elasticized regions 225, 226, 227 may be appropriately varied depending on the tensile stress required by each of the respective elasticized regions 225, 226, 227. For example, if it is desired to use the first and second waist elastic elements 230, 231 formed by the same elements even though the second elasticized region 226 requires an elongation percentage higher than that of the first elasticized region 225, the pitch at which the second waist elastic elements 231 are arranged must be necessarily set to be smaller than the pitch at which the first waist elastic elements 230 are arranged.

Instead of providing the respective elasticized regions 225, 226, 227 with the associated waist elastic elements 230, 231, 232 as the illustrated embodiment is the case, it is also possible to attach elastically stretchable/contractible sheet members on the inner surface of the annular waist panel 211 or to form the annular waist panel 211 directly by such elastically stretchable/contractible sheet members in order to assure each of the elasticized regions 225, 226, 227 to have the desired levels of tensile stress, respectively.

Referring again to FIG. 4, the rear waist panel 217 is formed with a pair of fourth elasticized regions 234 lying aside inward from the respective third elasticized region 227. The respective fourth elasticized regions 234 are provided with the fourth waist elastic elements 235 formed by the same elastic elements as the third waist elastic elements 232 used for the third elasticized region 227. As shown, the number of the fourth waist elastic elements 235 is fewer than any other waist elastic elements 230, 231, 232 and the tensile stress of the fourth elasticized region 234 as measured in the transverse direction Y is set to be lower than the tensile stress of any other elasticized regions 225, 226, 227.

The fourth elasticized regions 234 arranged in this manner are well adapted to cover a desired range of the wearer's buttock and thereby to define smoothly curved contact surface along the rounded surface of the wearer's buttock.

Various types of material widely used in the technical field of such disposable diaper may be used without limitation as stock materials for the respective members defining the front and rear waist panels 216, 217 and the absorbent chassis 212. While the elastic waist panel 211 comprises nothing but the front and rear waist panels 216, 217 in the illustrated embodiment, it may be contemplated that the elastic waist panel 211 comprises, in addition to the front and rear waist panels 216, 217, a crotch member extending between the front and rear waist panels 216, 217 to define the crotch region 215 or the front and rear waist panels 216, 217 are integrally contiguous to the crotch member. The present invention on the first aspect thereof is applicable not only to so-called pants-type disposable diaper of which the front and rear waist regions are previously joined together along the opposite side edges 219, 220 also to so-called open-type diaper.

The present invention on the second aspect thereof will be exemplarily described in reference to the accompanying drawings.

Figure 6:
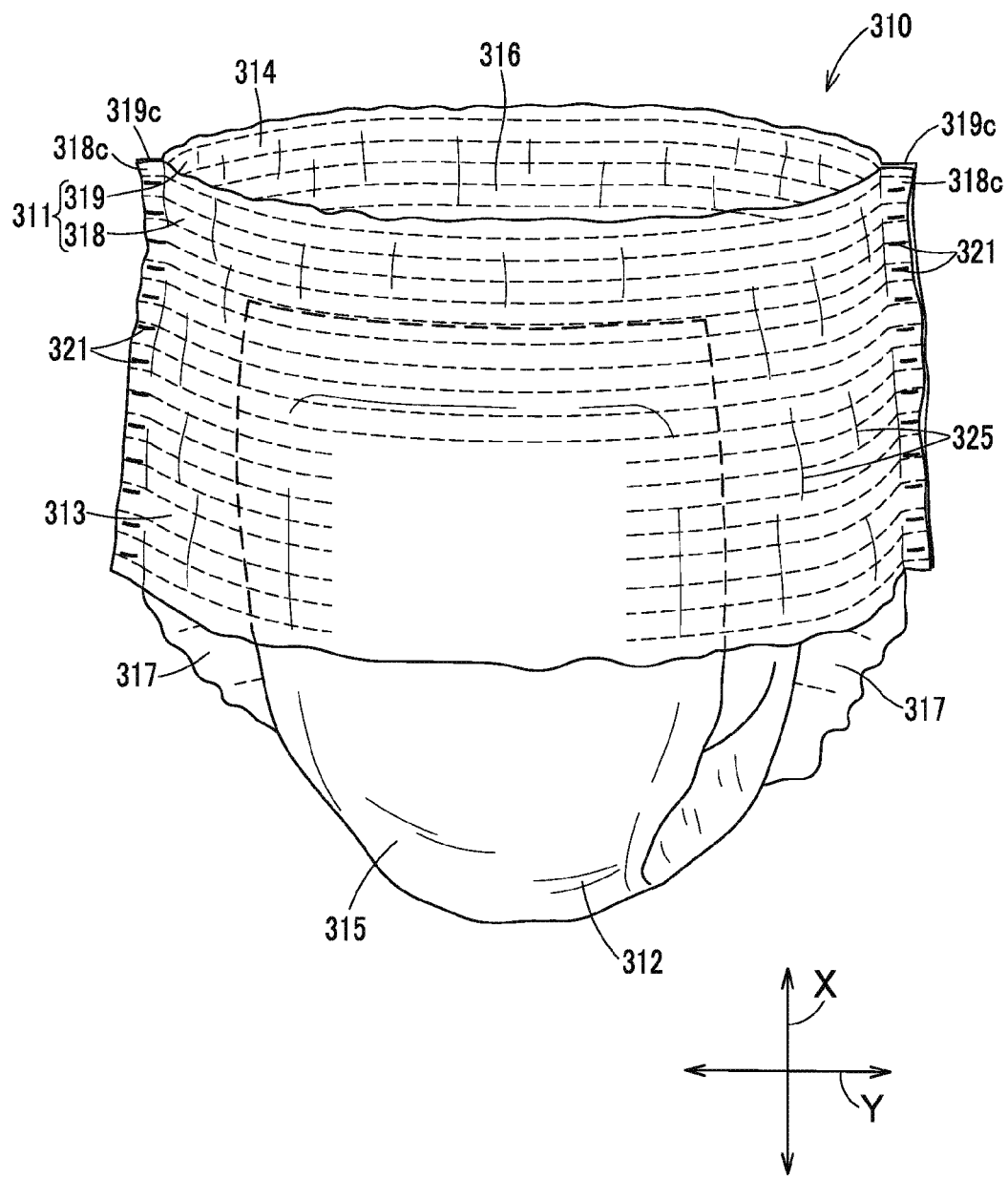
[FIG. 6] Perspective view of the diaper according to the invention on the second aspect thereof.
Figure 7:
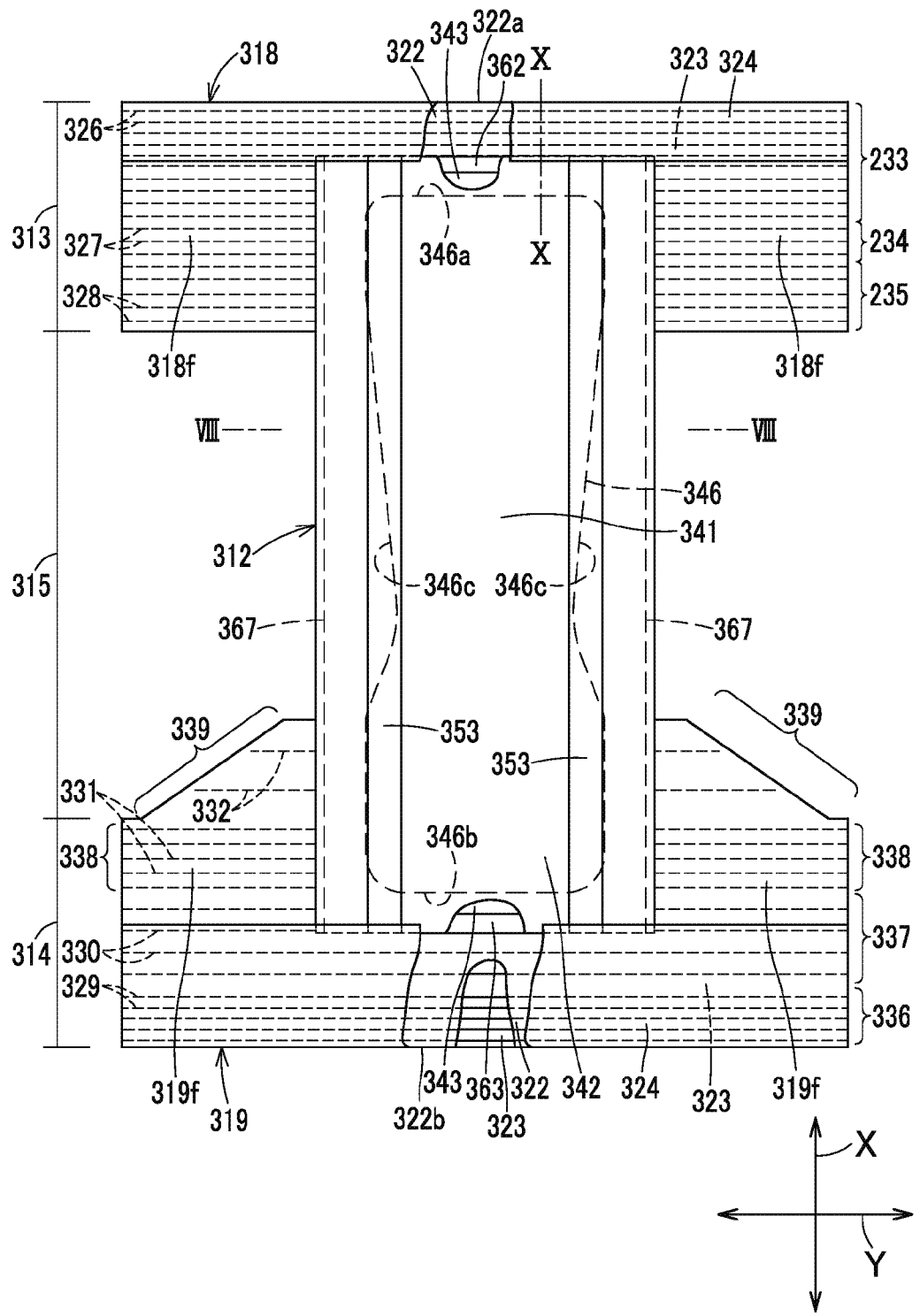
[FIG. 7] Plan view of the flatly developed disposable diaper of FIG. 6.
Figure 8:
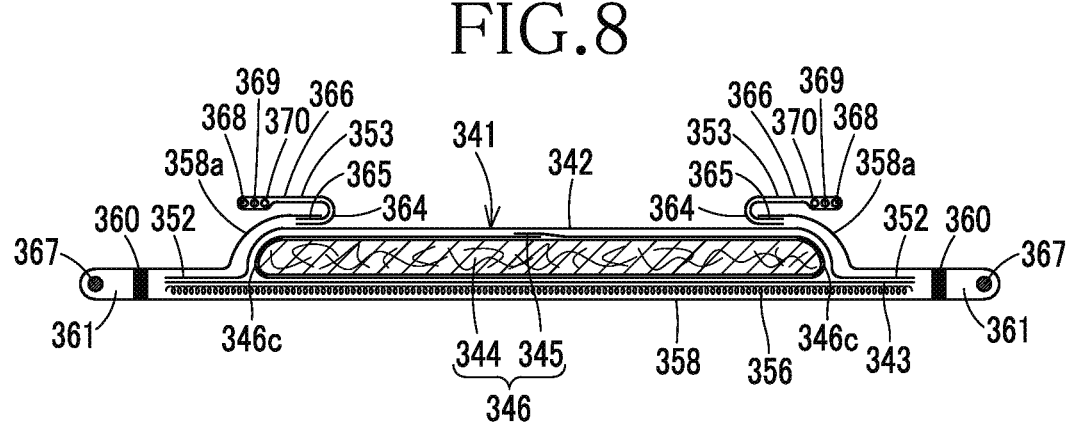
[FIG. 8] Sectional view of the disposable diaper taken along the line VIII-VIII.
Figure 9:
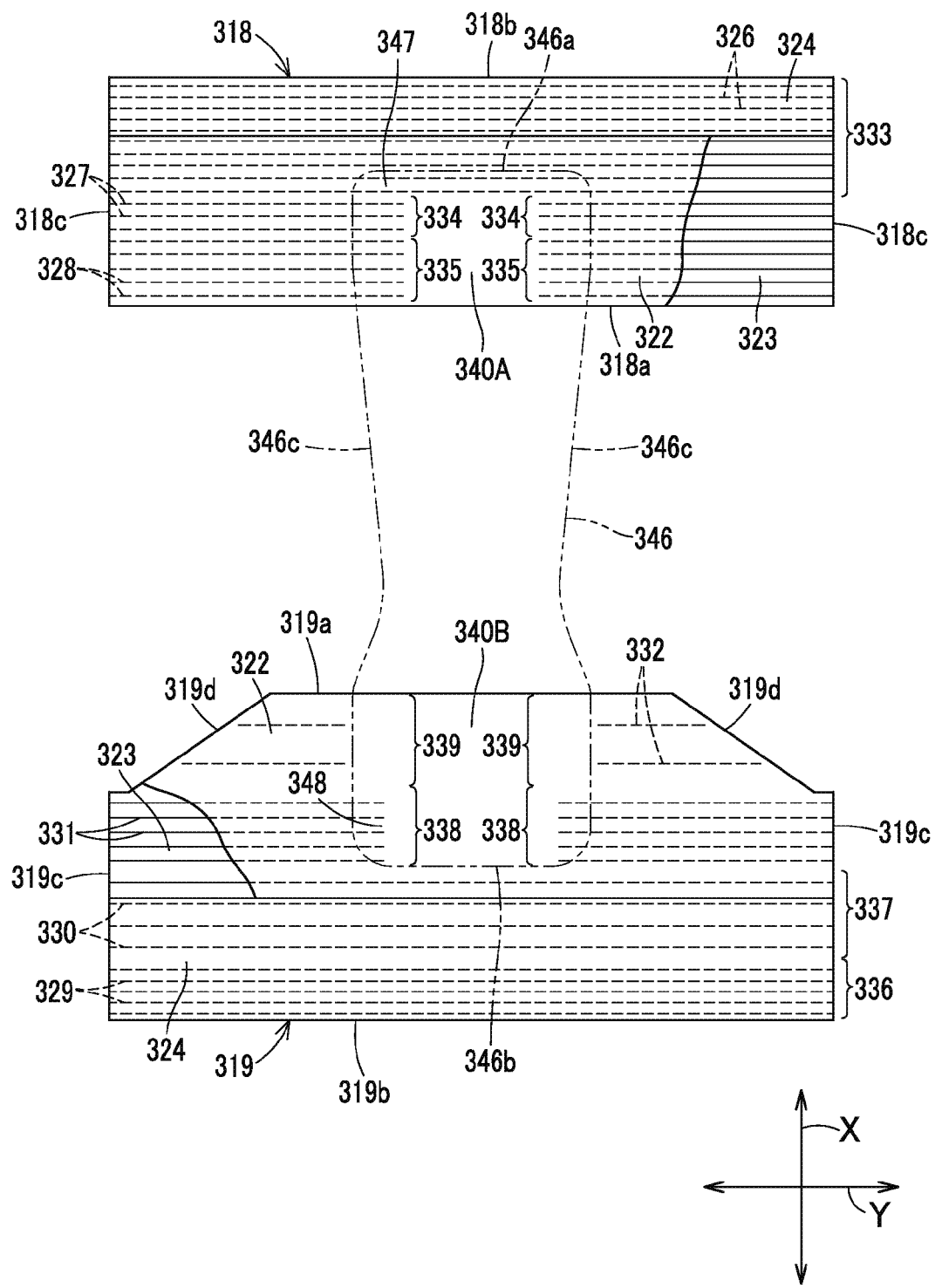
[FIG. 9] Plan view corresponding to FIG. 7 devoid of the absorbent chassis (except the absorbent panel).

FIG. 6 is a perspective view showing the diaper 310 as put on the wearer's body. FIG. 7 is a plan view showing the diaper 310 flatly developed in a longitudinal direction X as well as in a transverse direction Y after front and rear waist regions have been peeled off from each other along seams 321 in the longitudinal direction X. FIG. 8 is a sectional view taken along a line VIII-VIII in FIG. 7. FIG. 9 is a plan view corresponding to FIG. 7 devoid of an absorbent chassis 312 (except an absorbent panel 346). In FIG. 9, the absorbent panel 346 is indicated by an imaginary line for convenience of illustration.

As shown by FIG. 6, the diaper 310 comprises an annular elasticized waist panel 311, a chassis 312 attached to the elasticized waist panel 311 on the side facing the wearer's skin, a front waist region 313, a rear waist region 314, a crotch region 315 extending in the longitudinal direction X between the front and rear waist regions 313, 314, a waist-opening 316 and a pair of leg-openings 317. The waist-opening 316 is defined by the elasticized waist panel 311.

Referring to FIGS. 7 and 9, the elasticized waist panel 311 comprises, in turn, a front waist panel 318 defining the front waist region 313 and a rear waist panel 319 defining the rear waist region 314 and a part of the crotch region 315. The front waist panel 318 has a substantially rectangular shape contoured by an inner end 318a, an outer end 318b and opposite side edges 318c connecting the inner and outer ends 318a, 318b to each other. The rear waist panel 319 has a substantially trapezoidal shape contoured by an inner end 319a, an outer end 319b, opposite side edges 319c extending inward from the outer end 319 and opposite oblique inner side edges 319d connecting the outer end 319b and the inner end 319a to each other. The opposite side edges 318c of the front waist panel 318 and the opposite side edges 319c of the rear waist panel 319 are put flat together and then joined together along seams 321 arranged intermittently in the longitudinal direction X by various heat sealing means of well known art such as heat embossing or supersonic sealing so as to define a pair of leg-openings 317 in cooperation with the elastic waist panel 311 (See FIG. 6).

The front and rear waist panels 318, 319 are formed by a laminate comprising an inner layer sheet 322 lying on the inner side and an outer layer sheet 323 lying on the outer side. The outer layer sheet 323 has prolongations 324 extending outward from front and rear ends 322a, 322b of the inner layer sheet 322 in the longitudinal direction X wherein these prolongations 324 are folded back on the inner side of the diaper 310 and the respective opposite lateral zones are joined to the lateral zones 318f, 319f of the front and rear waist regions (i.e., opposite lateral regions of the front and rear waist panels) after the absorbent chassis 312 has been attached to the respective sides facing the wearer's skin of the front waist panels 318 and the rear waist panel 319. The prolongations 324 of the outer layer sheet 323 cover the front and rear ends 322a, 322b of the inner layer sheet 322 in this manner and thereby it is ensured to prevent body waste from leaking out beyond the front and rear ends 322a, 322b.

Suitable stock material for the inner layer sheet 322 and the outer layer sheet 323 includes hydrophobic fibrous nonwoven fabric, moisture-pervious plastic film and laminate sheet thereof.

First-seventh waist elastic elements 326, 327, 328, 329, 330, 321, 332 are sandwiched between the outer and inner layer sheets 323, 322 of the front and rear waist panels 318, 319 and attached to the inner surface of at least the inner layer sheet 322. As will be described more in details, under the effect of these waist elastic elements 326, 327, 328, 329, 330, 331, 332, the front waist region 313 is formed with first~third elasticized regions 333, 334, 335 and the rear waist region 314 is formed with fourth-seventh elasticized regions 336, 337, 338, 339. The diaper 310 is formed on its surface with a plurality of wrinkles 325 under contraction of these waist elastic elements 326, 327, 328, 329, 330, 331, 332 (See FIG. 6).

As shown in FIGS. 7 and 8, the absorbent chassis 312 includes an absorbent structure 341. The absorbent structure 341 comprises, in turn, a liquid-pervious liner 342 facing the wearer's skin (i.e., topsheet), a liquid-impervious backsheet 343, an absorbent panel 346 comprises an absorbent core 344 having an adequate bodily fluid absorbing capacity and a liquid-dispersant sheet 345 used to wrap an absorbent core 344.

The liquid-absorbent structure 341 comprises a pair of end flaps formed by bonding portions of the backsheet 343 extending outward beyond the front and rear ends 346a, 346b of the absorbent panel 346 in the longitudinal direction X to portions of the liner 342 facing the wearer's skin extending outward further than the backsheet 343 in the longitudinal direction X by hot melt adhesive (not shown) so as to extend in the transverse direction Y, a pair of inner side flaps 352 formed by bonding portions of the liner 342 facing the wearer's skin extending outward beyond a pair of side edges 346c of the absorbent panel 346 in the transverse direction Y to the corresponding portions of the backsheet 343 by hot melt adhesive (not shown) and a pair of barrier leg-cuffs 353 extending in the longitudinal direction X along opposite side edges of the liquid-absorbent structure 341.

The absorbent chassis 312 further includes a first sheet member 358 fixed to a lower surface of the liquid-absorbent structure 341 via a hot melt adhesive coated region 356 and a pair of sleeve-like outer side flaps 361 each comprising a region (prolongation) 358a of the first sheet member 358 extending outward beyond the liquid-absorbent structure 341 in the transverse direction Y, then folded back inward so as to define two layers placed upon each other, which are bonded to each other by hot melt adhesive 360. Each of these outer side flaps 361 is adapted to cover the outer side edge of the associated inner side flap 352. By cover the outer side edges of the respective inner side flaps 352 with the respective outer side flaps 361, it is ensured to prevent the outer side edges of the respective inner side flaps 352 which have conventionally been exposed in the form of relative sharp cut ends from coming in contact with and irritating the wearer's skin, causing itch and/or rash.

The absorbent chassis 312 further includes the front and rear end flaps 362, 363 defined by portions of the liner 342 facing the wearer's skin extending outward beyond the backsheet 343 in the longitudinal direction X and the front and rear ends of the first sheet member 358, respectively. These front and rear end flaps 362, 363 can be formed in this manner since the first sheet member 358 has previously been fixed to the lower surface of the liquid-absorbent structure 341.

To inner walls of the sleeves defined by the respective outer side flaps 361, strand-like elastic elements 367 stretchably/contractibly extending in the longitudinal direction X are attached by hot melt adhesive (not shown). In this way, with the diaper 310 put on the wearer's body, the outer side flaps 361 are curved inwardly as viewed in the transverse direction Y under contraction of the elastic elements 367 so as to be elastically pressed against the wearer's thighs. While each of the sleeves is provided with the single elastic element 367 so far as the illustrated embodiment is concerned, it is possible to provide each of the sleeves with two or more elastic elements 367.

Each of the barrier leg-cuffs 353 is formed by the prolongation 358a of the first sheet member 358 and the second sheet member 364 folded in two wherein the folded end of the second sheet member 364 is fixed to the prolongation 358a by hot melt adhesive (not shown) to define a fixed edge 365 and the distal end of the second sheet member 364 is folded back to define a sleeve-like free edge 366. With the diaper 310 flatly developed, the free edge 366 faces the associated prolongation 358a of the first sheet member 358 and the free edge 366 is provided on its inner surface with three elastic elements 368, 369, 370 permanently bonded thereto by hot melt adhesive (not shown) so as to extend in the longitudinal direction X. With the diaper 310 put on the wearer's body, the elastic elements 368, 369, 370 are sufficiently stretched to be spaced from the associated prolongation 358a and thereby body waste can be prevented from leaking out beyond the associated lateral region of the absorbent chassis 312.

While each of the free edges 366 is provided within the sleeve defined thereby with three elastic elements 368, 369, 370 in the case of the illustrated embodiment, the sleeve defined by the free edge 366 may be provided with at least one elastic element so far as this single elastic element has a tensile stress sufficient to space the free edge 366 from the associated prolongation 358a of the first sheet member 358. These elastic elements 368, 369, 370 may be replaced by an elastically contractible single sheet having a required width as the second sheet member 364.

In the absorbent panel 346, the absorbent core 344 comprises fluff pulp, super-absorbent polymer (SAP) and, if desired, heat sealable staple fiber mixed together and wrapped with the liquid-dispersant sheet 345 as a whole. By wrapping the absorbent core 344 as a whole with the liquid-dispersant sheet 345 in this manner, the absorbent core 344 can be protected from getting out of its desired shape and falling off of SAP. To improve the shape retention and the liquid dispersion, the absorbent core 344 is compressed to have a concave-shaped contour curved inwardly and provided with rigidity sufficiently higher than that of the sheet members constituting the diaper 310 to be sometimes referred to as "semi-rigid".

Referring again to FIGS. 6 and 9, the front waist panel 318 comprises the first elasticized region 333 defined between the outer end 318b and a front end 347 of the absorbent panel 346 so as to extend in the transverse direction X between the opposite side edges 318c, a pair of the second elasticized regions 334 defined adjacent the first elasticized region 333 so as to be spaced from and opposed to each other in the transverse direction Y, a pair of the third elasticized regions 335 defined adjacent the second elasticized regions 334 so as to be spaced from and opposed to each other in the transverse direction Y and a first non-elasticized region 340A defined in the middle of the front waist region 313 as viewed in the transverse direction Y and spacing the respective second elasticized regions 334 from the respective third elasticized regions 335.

The first elasticized region 333 is provided with a plurality of the first waist elastic elements 326 extending in the transverse direction Y between the opposite side edges 318c of the front waist panel 318, the second elasticized regions 334 are provided with the second waist elastic elements 327 extending from the side edges 318c to opposite side edges of a front end region 347 of the absorbent panel 346, and the third elasticized regions 335 are provided with the third waist elastic elements 328 extending, just as the second waist elastic elements 328, from the side edges 318c to the opposite side edges of the front end region 347 of the absorbent panel 346.

The first non-elasticized region 340A defined in the middle of the front waist panel 318 as viewed in the transverse direction Y may be formed as will be described below. For example, according to so-called "cut back method" conventionally used for the disposable diaper as described herein, the second and third waist elastic elements 327, 328 are cut back. Specifically, the regions corresponding to the second and third elasticized region 334, 335 are coated with hot melt adhesive in appropriate patterns but the region corresponding to the first non-elasticized region 340A is left not coated with hot melt adhesive. Then, the second and third waist elastic elements 327, 328 are fed under tension toward these regions 334, 335, 340A and attached under tension thereto in the regions coated with the hot melt adhesive. Now respective segments of the second and third waist elastic elements 327, 328 free from the effect of the hot melt adhesive are cut in the first non-elasticized region 340A. Thereupon, these segments of the elastic elements 327, 328 automatically contract (so-called "cut back") toward the fixed segments of these elastic elements 327, 328. Consequently, there are substantially neither the second waist elastic elements 327 nor the third waist elastic elements 328 under tension in the region corresponding to the first non-elasticized region 340A. It is also possible to form the first non-elasticized region 340A by removing the segments lying in the region corresponding to the first non-elasticized region 340A after the second and third waist elastic elements 327, 328 have been fed to the respective regions 334, 335, 340A.

Further alternatively, it is also possible to for the first non-elasticized region 340A by attached the second and third waist elastic elements 327, 328 not under tension by hot melt adhesive and then by depriving or restraining the elasticity thereof.

The term "non-elasticized region" used herein refers to a region in which substantially none of the elastic elements is present or a region in which no elasticity of the elastic elements is developed.

The first non-elasticized region 340A formed in this manner makes it possible to attach a plastic sheet printed with graphics to the inner surface of the first non-elasticized region 340A so that the graphics would be visible through the first non-elasticized region 340A. The middle region of the absorbent panel 346 is not affected directly by contractile force of the elastic elements and therefore the middle region of the absorbent panel 346 would not be readily deformed, for example, in the form of wrinkles and the absorbing capacity of the absorbent core would not be reduced.

As illustrated, a pitch at which the first, second and third waist elastic elements 326, 327, 328 are arranged in the longitudinal direction X, respectively, is uniform. In addition, the second elasticized region 334 is set to have an elongation percentage higher than that of the third elasticized region 335 and equal to or higher than that of the first elasticized region 333 while the second elasticized region 334 is set to have an elongation percentage higher than that of the first elasticized region 333 and equal or higher than that of the third elasticized region 335. Thus, the correlation of the first, second and third elasticized regions 333, 334, 335 with respect to the tensile stress thereof can be represented by an inequality: the second elasticized region 334≧the first elasticized region 333>the third elasticized region 335. The correlation among the first, second and third elasticized regions 333, 334, 335 with respect to the elongation percentage can be represented by an inequality: the second elasticized region 334≧the third elasticized region 335>the first elasticized region 333.

More specifically, the first elasticized region 333 preferably has a tensile stress of 38-42 mN/mm at 65% of the maximum elongation, the second elasticized region 334 preferably has a tensile stress of 42-48 mN/mm at 65% of the maximum elongation and the third elasticized region 335 preferably has a tensile stress of 28-32 mN/mm at 65% of the maximum elongation.

The tensile stress of the respective elasticized regions 333, 334, 335 was measured by a method as follows:

First, the waist regions are peeled off from each other along the seams 321 and the diaper 310 is flatly developed as seen in FIG. 7 and the respective elastic elements 326, 327, 328 are stretched to the maximum elongation in the transverse direction Y. The front waist panel 318 as a whole is cut off from the diaper 310 and then the respective elasticized regions 333, 334, 335 are cut away from this front waist panel 318 to obtain desired test pieces. Based on these test pieces, widths (dimensions in the longitudinal direction Y of the diaper 310) of the respective test pieces are measured. The respective elasticized regions 333, 334, 335 are cut off in the region defined between each pair of the adjacent elastic elements 326, 327, 328 in middle of this region as viewed in longitudinal direction X. Then, each of the test pieces in contracted state is fixed between a pair of chucks of Tensile Tester manufactured by Shimadzu Corporation (a distance between these chucks is initially set to 100 mm and appropriately adjusted depending on the each of the test pieces). Now the test piece is stretched in the transverse direction Y of the diaper 310 at a rate of 100 mm/min and a load (mN) at 65% of the maximum elongation is measured. Thus, tensile stress is calculated for each of the elasticized regions 333, 334, 335 according to an equation:

Measured value (mN)÷region width (mm)=tensile stress.

To meet the correlation among the respective elasticized regions 333, 334, 335 with respect to tensile stress as well as elongation percentage thereof as have been described above, the second waist elastic element 327 may have a sectional area larger than that of the third waist elastic element 328 and equal to or larger than that of the first waist elastic element 326 and an elongation percentage equal to that of the third waist elastic element 328 but higher than that of the first waist elastic element 326.

More specifically, as the waist elastic elements 326, 327, 328, strand-like rubber elastic elements may be employed wherein the first waist elastic elements 326 may have a sectional area of 550-650 dtex and an elongation percentage of 250~300%, the second waist elastic element 327 may have a sectional area of 550-650 dtex and an elongation percentage of 300-350% and the third waist elastic element 328 may have a sectional area of 450-500 dtex and an elongation percentage of 300-350%.

The correlation as has been described above with respect to the tensile stress may be met also by forming the first, second and third waist elastic elements 326, 327, 328 from the same elastic elements so far as the number and the pitch thereof are appropriately adjusted. For example, when the first waist elastic elements 326 and the second waist elastic elements 327 are formed by the same elastic elements, the pitch for the second waist elastic elements 327 may be selected to be smaller than the pitch for the first waist elastic elements 326 to make the tensile stress of the second elasticized region 334 higher than the tensile stress of the first elasticized region 333.

The arrangement described just above such that the first elasticized region 333 extends across the front end 347 of the absorbent panel 346 in the transverse direction Y and the second elasticized regions 334 extending on the opposite lateral zones of the front end 347 of the absorbent panel 346 have the tensile stress higher than those of the other elasticized regions 333, 335 ensures the front end 347 of the absorbent panel 346 to be held in close contact with the wearer's body without being unintentionally displaced from its desired position. In addition, the second elasticized regions 334 have the elongation percentage higher than that of the first elasticized region 333 so that the second elasticized regions 334 are not affected directly by stretching and/or contraction of the first elasticized region 333.

The rear waist panel 319 comprises the fourth elasticized region 336 extending along between the opposite side edges 319c along the outer end 319b, the fifth elasticized region 337 defined adjacent the fourth elasticized region 336 so as to extend to the rear end 346b of the absorbent panel 346, a pair of the sixth elasticized regions 338 defined adjacent the fifth elasticized region 337 so as to be spaced from and opposed to each other in the transverse direction Y, a pair of the seventh elasticized regions 339 defined adjacent the respective sixth elasticized regions 338 so as to extend to the inner end 319a be spaced from and opposed to each other in the transverse direction Y, and a second non-elasticized region 340B defined between the respective sixth elasticized regions 338 and the respective seventh elasticized regions 339.

The fourth and fifth elasticized regions 336, 337 are provided with the fourth and fifth waist strand-like elastic elements 329, 330 extending between the opposite side edges 319c in the transverse direction Y, respectively, the respective sixth elasticized regions 338 are provided with the sixth waist strand-like elastic elements 331 extending from the opposite side edges 319c to the lateral zones of the front end 347 of the absorbent panel 346, and the respective seventh elasticized regions 339 are provided with the seventh waist strand-like elastic elements 332 extending from the opposite side edges 319c to the vicinity of the opposite side edges 346c of the absorbent panel 346.

The second non-elasticized region 340B may be formed by the same method as used to form the first non-elasticized region 340A. Specifically, the elastic elements may be cut in the region corresponding to the second non-elasticized region 340B or removed from this region so that substantially none of the elastic elements is present in this region. Alternatively, the segments of the elastic elements remaining in this region may be deprived of elasticity thereof to form the second non-elasticized region 340B.

In the rear waist panel 319, each of the sixth elasticized regions 338 is set to exhibit a tensile stress same as or higher than a tensile stress of the fourth elasticized region 336, the tensile stress of the fourth elasticized region 336 is set to be higher than a tensile stress of the fifth elasticized region 337, and the tensile stress of the fifth elasticized region 337 is set to be higher than a tensile stress exhibited by each of the seventh elasticized region 339. As for the elongation percentage, the fifth elasticized region 337 is set to exhibit an elongation percentage equal to an elongation percentage exhibited by each of the sixth elasticized regions 338. This elongation percentage common to the fifth and sixth elasticized regions 337, 338 is set to be higher than an elongation percentage of the fourth elasticized region 336 and the elongation percentage of the fourth elasticized region 336 is set to be higher than an elongation percentage exhibited by each of the seventh elasticized regions 339. Accordingly, the correlation among the fourth-seventh elasticized regions 336, 337, 338, 339 with respect to the tensile stress may be represented by an inequality: the sixth elasticized region 338≧the fourth elasticized region 336>the fifth elasticized region 337>the seventh elasticized region 339. The correlation among these elasticized regions with respect to the elongation percentage may be given by an expression: the fifth elasticized region 337=the sixth elasticized region 338>the fourth elasticized region 336>the seventh elasticized region 339.

More specifically, the fourth elasticized region 336 preferably has a tensile stress of 38-42 mN/mm at 65% of the maximum elongation, the fifth elasticized region 337 preferably has a tensile stress of 8-20 mN/mm at 65% of the maximum elongation, the sixth elasticized region 338 preferably has a tensile stress of 42-48 mN/mm at 65% of the maximum elongation and the seventh elasticized region 339 preferably has a tensile stress of 1-4 mN/mm at 65% of the maximum elongation.

Tensile stress of the respective elasticized regions 336, 337, 338, 339 may be measured by the same method as used for the first, second and third elasticized regions 333, 334, 335 except for the seventh elasticized region 339. This region 339 includes the inner side edges 319d obliquely extending inward with respect to the diaper 310 and therefore opposite ends of this region 339 can not be fixed by chucks of the Tensile Tester. To overcome this problem, the seventh elasticized region 339 is cut off from the article and then a sub-region defined between a pair of the seventh waist elastic elements 332 and a sub-region defined between the seventh waist elastic element 332 and the inner end 319a are cut off from the seventh elasticized region 339 to obtain two test pieces. The test pieces obtained in this manner are respectively stretched by the Tensile Tester in a direction corresponding to the transverse direction Y of the diaper 310 to measure respective stress values at 65% of the maximum elongation. The stress values measured on these two sub-regions are summed up to obtain the tensile stress of the seventh elasticized region 339.

To set each of the fourth-seventh elasticized regions 336, 337, 338, 339 to exhibit desired tensile stress and elongation percentage, the waist elastic elements 329, 330, 331, 332 are provided in the form of strand-like elastic elements wherein the fourth waist elastic elements 329 may have a sectional area of 550-650 dtex and an elongation percentage of 250-300%, the fifth waist elastic element 330 may have a sectional area of 500-550 dtex and an elongation percentage of 300-350%, the sixth waist elastic element 331 may have a sectional area of 550-650 dtex and an elongation percentage of 300-350%, and the seventh elasticized region 332 may have a sectional area of 500-550 dtex and an elongation percentage of 180-240%.

According to the illustrated embodiment, the pitch at which the sixth waist elastic elements 331 are arranged is larger than the pitch at which the fourth waist elastic elements 329 are arranged, the pitch at which the fifth waist elastic elements 330 are arranged is larger than the pitch at which the sixth waist elastic elements 331 are arranged, and the pitch at which the seventh waist elastic elements 332 are arranged is larger than the pitch at which the fifth waist elastic elements 330 are arranged. The pitches may be correlatively adjusted in this manner to achieve the desired correlation among the respective elasticized regions 336, 337, 338, 339 with respect to the elongation percentage. Appropriate adjustment of the pitches at which the respective elastic elements are arranged makes it possible also to use uniform elastic elements as the fourth-seventh waist elastic elements 329, 330, 331, 332. So far as the desired correlation is established among the respective elasticized regions 336, 337, 338, 339, the fifth waist elastic elements 330 lying aside toward the sixth elasticized region 338 may have the elongation percentage equal to the elongation percentage of the sixth waist elastic elements 331 and/or the sixth waist elastic elements 331 may have the elongation percentage equal to the elongation percentage of the seventh waist elastic elements 332.

The unique arrangement such that the sixth elasticized region 338 extending on the opposite lateral zones of the rear end 348 of the absorbent panel 346 has a tensile stress higher than those of the other elasticized regions 336, 337, 339 assures the rear end 348 of the absorbent panel 346 to be held in close contact with the wearer's body without being unintentionally displaced from the desired position. The additional unique arrangement such that the sixth elasticized region 338 exhibits an elongation percentage higher than an elongation percentage exhibited by the fourth elasticized region 336 assures the sixth elasticized region 338 to be independent from stretching and/or contraction of the fourth elasticized region 336.

As shown, the number of the seventh waist elastic elements 332 is fewer than those of the other waist elastic elements 329, 330, 331 and the seventh waist elastic elements 339 exhibit the tensile stress lower than those of the other elasticized regions 336, 337, 338. This unique arrangement assures that the seventh elasticized region 332 reliably covers a desired area of the wearer's buttock and provides soft frilly contact surface in conformity with the curve of the buttock.

Figure 10:
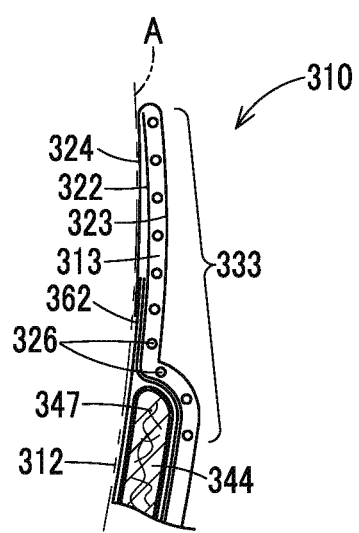
[FIG. 10] Sectional view taken along the line X-X in FIG. 7, showing the disposable diaper put on the wearer's body.

FIG. 10 is a schematic sectional view taken along a line X-X in FIG. 7, assuming that the disposable diaper 310 has been put on the wearer's body. FIG. 11A, 11B is a schematic sectional view corresponding to FIG. 10 showing the disposable diaper 110 of prior art.

As shown by FIG. 10, the first waist elastic elements 326 defining first elasticized region 333 of the front waist region 313 extend across the front end flap 362 of the absorbent chassis 312 as well as the front end 347 of the absorbent panel 346. The first elasticized region 333 extending across the front flap 362 of the absorbent chassis 312 as well as the front end 347 of the absorbent panel 346 in this manner make it possible to prevent the front waist region 313 from being partially formed with a step.

In the case of the conventional disposable diaper 110, as will be apparent from FIG. 11A, a space S has been inevitably formed between the front end flap 162 of the absorbent chassis 112 and the wearer's body A. This is for the reason that the absorbent core 144 typically contains fluff pulp for the purpose of improvement in liquid-absorbing capacity as well as dispersant capacity thereof and has a given thickness larger than that of the front end flap 162 consisting of only the sheet member. Such differential thickness inevitably causes the region defined between the waist-opening's periphery 116a provided with the waist elastic elements 126 so as to be brought into close contact with the wearer' body A and the absorbent core 144 to be spaced from the wearer's body A. Particularly when a large quantity of urine is absorbed by the absorbent core 144, the thickness of the absorbent core 144 will further increase and the space S will be correspondingly enlarged.

If the wearer changes his or her posture, e.g., bends him- or herself forward from the above-described situation, the wearer's body A depresses the waist-opening's periphery 116a and the vicinity thereof forward with respect to the wearer so as to fold the front end flap 162 and the region of the waist member 111 opposed to the front end flap 162 toward the space S. As a result, the front end flap 162 and the region of the waist member 111 facing the front end flap 162 are displaced together downward into the interface between the wearer's body A and the absorbent core 144, as shown by FIG. 11B, resulting in formation of a step R.

Even when the waist elastic elements 126 extend across the front flap 162, the absorbent core 144 may be inevitably thickened as a quantity of urine thereby absorbed increases. Consequentially, the front end 147 of the absorbent panel 146 and the region of the waist member 111 facing the front end 147 maybe displaced upward onto the front end flap 162 kept in close contact with the wearer's body A, eventually leading to the situation in which the front end flap 162 of the absorbent panel 146 and the region of the waist member 111 facing the front end flap 162 are displaced downward into the space S, i.e., the situation illustrated by FIG. 11B.

If the step R is formed, it will result not only in that the diaper 110 would be displaced from the desired position but also in that an excessive quantity of urine for a given absorbing capacity of the absorbent core 144 might stay in the step R and eventually leak out from the diaper 110. In addition, the step R may disfigure the diaper 110.

Particularly when the annular elasticized waist panels 311 and the absorbent chassis 312 inclusive of the absorbent core 344 are separately formed as in the present embodiment, the absorbent chassis 312 is suspended between the annular elasticized waist panels 311. In such situation, the absorbent chassis 312 might be undesirably displaced between the elastic waist panels 311 and a possibility that the step R might be formed will be higher than the case of the diaper 310 having the absorbent core 344 sandwiched directly between the elastic waist panels 311.

To overcome such problem, according to the present embodiment, the first waist elastic elements 326 extend across the front end 347 of the absorbent chassis 312. This unique arrangement is effective to prevent the front flap 362 and a region of the front waist panel 318 facing to the front flap 362 from being displaced downward into the space S. The first waist elastic elements 326 extend also across the front end 347 of the absorbent panel 346 and the tensile stress thereof kee
the front end 347 of the absorbent panel 346 in close contact with the wearer's body A and restrains an upward movement thereof so as to prevent the front waist region 313 from being partially formed with the undesirable step R.

As has previously been described, the respective second elasticized regions 334 having the tensile stress higher than those of the first and third elasticized regions 333, 335 extend on the opposite lateral zones of the front end 347 of the absorbent panel 346. With such unique arrangement, the opposite lateral zones of the front end 347 can be reliably held in close contact with the wearer's body A and the first elasticized region 333 cooperates with the second elasticized region 334 to prevent the front end 347 of the absorbent panel 346 from being undesirably displaced upward.

To keep the front end 347 of the absorbent panel 346 in close contact with the wearer's body A by means of the first elasticized region 333 and the second elasticized region 334, the absorbent core 344 preferably has a rigidity in a range of 0.03-0.15 N·cm as measured by Taber method. If the rigidity of the absorbent core 344 exceeds 0.15 N·cm, the front end 347 of the absorbent panel 346 might not be able to be kept in close contact with the wearer's body A even when the tensile stress of the first and second elasticized regions 333, 334 are exerted thereon.

It should be appreciated here that the respective elasticized regions 333, 334, 335, 336, 337, 338, 339 may have desired tensile stresses, respectively, not only by providing them with the strand-like elastic elements but also by attaching an elastically stretchable/contractible sheet to the inner surface of the annular waist panel 311 or by using a sheet member having in itself a desired elasticity as the annular elasticized waist panel 311.

Various types of material widely used in the technical field of such disposable diaper may be used without limitation as stock materials for the respective members defining the front and rear waist panels 318, 319 and the absorbent chassis 312. While the elastic waist panel 311 comprises nothing but the front and rear waist panels 318, 319 in the illustrated embodiment, it may be contemplated that the elastic waist panel 311 comprises, in addition to the front and rear waist panels 318, 319, a crotch member extending between the front and rear waist panels 318, 319 to define the crotch region 315 or the front and rear waist panels 318, 319 are integrally contiguous to the crotch member. The present invention on the second aspect thereof is applicable not only to so-called pants-type disposable diaper of which the front and rear waist regions are previously joined together along the opposite side edges 318c, 319c of the front and rear waist regions 313, 314 also to so-called open-type diaper.

The invention claimed is:

1. A disposable diaper having, relative to a wearer, a longitudinal direction, a transverse direction, a side facing said wearer's skin, a side facing away from said wearer's skin, said disposable diaper comprising:
an annular elasticized waist panel defining a waist opening, a front waist region and a rear waist region;
an absorbent chassis joined to said waist panel and extending into said front and rear waist regions, said absorbent chassis defining a crotch region extending between said front and rear waist regions and including an absorbent core and front and rear end flaps extending from front and rear ends of said absorbent core in said longitudinal direction;
at least said front waist region of said front and rear waist regions including elasticized regions extending at least in said transverse direction;
said elasticized regions including a first elasticized region, a second elasticized region and a pair of third elasticized regions, said first elasticized region located between a periphery of said waist-opening and said front end flap of said absorbent chassis, said second elasticized region located adjacent said first elasticized region and extending across said front end flap of said absorbent chassis, said pair of third elasticized regions located adjacent said second elasticized region, each of said third elasticized regions extending from opposite side edges of said front waist region to opposite side edges of said absorbent chassis, said third elasticized regions being spaced from and opposed to each other in said transverse direction on both sides of a non-elasticized region located in a transverse middle portion of said front waist region,
wherein said rear waist region includes a pair of fourth elasticized regions extending in the longitudinal direction on opposite sides of a rear non-elasticized region located in a transverse middle portion of the rear waist panel,
said fourth elasticized regions having a tensile stress in said transverse direction that is lower than a tensile stress in said transverse direction of any of said first, second and third elasticized regions.

2. The disposable diaper according to claim 1 wherein said first elasticized region extends in the transverse direction across substantially the entire length of the front waist region.

3. The disposable diaper according to claim 1 wherein said second elasticized region extends in the transverse direction across substantially an entire length of said front waist region.

4. The disposable diaper according to claim 1 wherein said front and rear waist regions both include said first, second and third elasticized regions.

5. The disposable diaper according to claim 1 wherein said elasticized regions include waist elastic elements extending longitudinally, said waist elastic elements being spaced at different pitches in said first, second and third elasticized regions.

6. The disposable diaper according to claim 1 wherein portions of said third elasticized regions extend over said absorbent core.

7. The disposable diaper according to claim 1 wherein said second elasticized region has a tensile stress greater than or equal to a tensile stress of said first elasticized region.

8. The disposable diaper according to claim 1 wherein said first elasticized region has a tensile stress greater than a tensile stress of said pair of third elasticized regions.

9. The disposable diaper according to claim 1 wherein said second elasticized region has an elongation percentage greater than or equal to an elongation percentage of said first elasticized region.

10. A disposable diaper having, relative to a wearer, a longitudinal direction X, a transverse direction Y, a side facing said wearer's skin, a side facing away from said wearer's skin, said disposable diaper comprising:
an annular elasticized waist panel defining a waist opening, a front waist region and a rear waist region;
an absorbent chassis defining a crotch region and including an absorbent structure joined to said waist panel and extending into said front and rear waist regions, said absorbent structure including an absorbent core and front and rear end flaps extending from front and rear ends of said absorbent core in said longitudinal direction;
at least said front waist region of said front and rear waist regions including elasticized regions extending at least in said transverse direction;
said elasticized regions including a first elasticized region, a pair of second elasticized regions, and a pair of third elasticized regions, said first elasticized regions located between a periphery of said waist-opening and a front end of said absorbent chassis inclusive of said front end flap, said first elasticized region extending across said front end of said absorbent panel, said pair of second elasticized regions located adjacent said first elasticized region and extending from opposite side edges of said front waist region to opposite side edges of a front end of said absorbent panel, said pair of second elasticized regions being spaced from and opposed to each other in said transverse direction on both sides of a first non-elasticized region located in a transverse middle portion of said front waist region, said pair of third elasticized regions located adjacent said second elasticized regions and extending from said opposite side edges of said front waist region to said opposite side edges of said front end of said absorbent panel, said pair of third elasticized regions being spaced from and opposed to each other in said transverse direction on both sides of said first non-elasticized region, said elasticized regions in said rear waist region further comprising:

a fourth elasticized region defined between opposite side edges of said rear waist region so as to extend along said periphery of said waist-opening in said transverse direction, a fifth elasticized region defined adjacent said fourth elasticized region so as to extend to said rear end of said absorbent panel, a pair of sixth elasticized regions defined adjacent said fifth elasticized region so as to be spaced from and opposed to each other in said transverse direction on both sides of a second non-elasticized region formed in a transverse middle of said rear waist region, and a pair of seventh elasticized regions defined adjacent said sixth elasticized regions so as to be spaced from and opposed to each other in said transverse direction on both sides of said second non-elasticized region, wherein said seventh elasticized regions have a tensile stress lower than a tensile stress of each of said fourth, fifth and sixth elasticized regions.

11. The disposable diaper according to claim 10 wherein said first elasticized region extends in the transverse direction across substantially the entire length of the front waist region.

12. The disposable diaper according to claim 10 wherein said rear waist region includes a fourth elasticized region, a fifth elasticized region and a pair of sixth elasticized regions.

13. The disposable diaper according to claim 12 wherein said fourth and fifth elasticized regions extend in the transverse direction substantially an entire length of said rear waist region.

14. The disposable diaper according to claim 10 wherein said elasticized regions include waist elastic elements extending longitudinally and defining a common pitch.

15. The disposable diaper according to claim 10 wherein portions of said pair of third elasticized regions extend partially over said absorbent core.

16. The disposable diaper according to claim 10 wherein said pair of second elasticized regions has a tensile stress greater than or equal to a tensile stress of said first elasticized region.

17. The disposable diaper according to claim 10 wherein said first elasticized region has a tensile stress greater than a tensile stress of said pair of third elasticized regions.

18. The disposable diaper according to claim 10 wherein said pair of second elasticized regions has an elongation percentage greater than or equal to an elongation percentage of said first elasticized region.

* * * * *

UNITED STATES PATENT AND TRADEMARK OFFICE
CERTIFICATE OF CORRECTION

PATENT NO.        : 8,518,009 B2
APPLICATION NO.   : 12/935495
DATED             : August 27, 2013
INVENTOR(S)       : Saito et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 363 days.

Signed and Sealed this
Fifteenth Day of September, 2015

Michelle K. Lee
*Director of the United States Patent and Trademark Office*